United States Patent
Yoo et al.

(10) Patent No.: US 7,838,036 B2
(45) Date of Patent: Nov. 23, 2010

(54) METHOD AND APPARATUS FOR ISOLATING AND PURIFYING NUCLEIC ACID USING A SINGLE SURFACE

(75) Inventors: Chang-eun Yoo, Yongin-si (KR); Sung-young Jeong, Yongin-si (KR); Young-rok Kim, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 12/716,695

(22) Filed: Mar. 3, 2010

(65) Prior Publication Data

US 2010/0160585 A1 Jun. 24, 2010

Related U.S. Application Data

(62) Division of application No. 11/693,259, filed on Mar. 29, 2007, now Pat. No. 7,718,371.

(30) Foreign Application Priority Data

Sep. 25, 2006 (KR) .................. 10-2006-0092921

(51) Int. Cl.
  *A61K 9/14* (2006.01)
  *A61K 9/16* (2006.01)
  *C12Q 1/68* (2006.01)
  *C07H 21/04* (2006.01)
  *C12Q 1/70* (2006.01)

(52) U.S. Cl. .................. 424/489; 424/490; 435/5; 435/6; 435/7.1; 435/7.2; 536/23.1

(58) Field of Classification Search .......... 424/489, 424/490; 435/5, 6, 7.1, 7.2; 536/23.1
See application file for complete search history.

(56) References Cited

U.S. PATENT DOCUMENTS

| 5,234,809 | A | 8/1993 | Boom et al. |
| 6,617,105 | B1 | 9/2003 | Rudi et al. |
| 6,830,784 | B2 | 12/2004 | Gutowski et al. |
| 2006/0110725 | A1 | 5/2006 | Lee et al. |
| 2006/0134675 | A1 | 6/2006 | Yoo et al. |
| 2006/0228737 | A1 | 10/2006 | Hwang et al. |
| 2006/0264621 | A1 | 11/2006 | Hwang et al. |
| 2007/0238114 | A1 | 10/2007 | Lee et al. |

FOREIGN PATENT DOCUMENTS

EP  1650297 A2  4/2006

(Continued)

OTHER PUBLICATIONS

Veyret, R., et al.; "Magnetic colloids for the generic capture of viruses"; Analytical Biochemistry; vol. 346; pp. 59-68; 2005.
Pompe, T. et al.; "Maleic Anhydride Copolymers-A Versatile Platform for Molecular Biosurface Engineering"; Biomacromolecules; vol. 4; pp. 1072-1079; 2003.

(Continued)

*Primary Examiner*—Jezia Riley
(74) *Attorney, Agent, or Firm*—Cantor Colburn LLP

(57) ABSTRACT

Provided is a method of isolating nucleic acid from cells using a single surface, wherein a compound represented by Formula 1 is bound to the surface. Also provided are an apparatus for isolation of nucleic acids, and a bead for isolating nucleic acids.

4 Claims, 1 Drawing Sheet

FOREIGN PATENT DOCUMENTS

| | | | |
|---|---|---|---|
| EP | 1655366 | A2 | 5/2006 |
| EP | 1662008 | A2 | 5/2006 |
| EP | 1715039 | A1 | 10/2006 |
| EP | 1724016 | A1 | 11/2006 |
| EP | 1842914 | A1 | 10/2007 |
| EP | 1870449 | A1 | 12/2007 |
| EP | 1876231 | A1 | 1/2008 |
| KR | 1020060058528 | A | 5/2006 |
| KR | 1020060070697 | A | 6/2006 |
| WO | 9851693 | A1 | 11/1998 |
| WO | 0248164 | A3 | 6/2003 |
| WO | 2004055213 | A1 | 7/2004 |
| WO | 2007149136 | A2 | 12/2007 |

OTHER PUBLICATIONS

European Search Report dated Feb. 5, 2008 for Application No. 07105732.7.

European Extended Search Report for Application No. EP 07105732.7 dated Oct. 15, 2009.

Lee, J. et al., Microchip-based one step DNA extraction and real-time PCR in one chamber for rapid pathogen identification, Lab Chip., 2006; 6 (7): pp. 886-895.

Liu, R.N. et al., Self-Contained, Fully Integrated Biochip for Sample Preparation, Polymerase Chain Reaction Amplification, and DNA Microarray Detection, Anal. Chem., 2004, 76 (7): pp. 1824-1831.

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: forward primer

<400> SEQUENCE: 1
yccakactcc tacgggaggc                                              20

<210> SEQ ID NO 2
<211> LENGTH: 22
<212> TYPE: DNA
<213> ORGANISM: Artificial Sequence
<220> FEATURE:
<223> OTHER INFORMATION: reverse primer

<400> SEQUENCE: 2
gtattaccgc ttctgctggc ac                                           22
```

METHOD AND APPARATUS FOR ISOLATING AND PURIFYING NUCLEIC ACID USING A SINGLE SURFACE

CROSS REFERENCE TO RELATED APPLICATIONS

This application is a division of U.S. patent application Ser. No. 11/693,259 filed Mar. 29, 2007, which claims the benefit of Korean Patent Application No. 10-2006-0092921 filed on Sep. 25, 2006, and all the benefits accruing therefrom under 35 U.S.C. §119, the disclosure of each of which is incorporated herein in its entirety by reference.

BACKGROUND OF THE INVENTION

1. Field of the Invention

The present invention relates to a method and apparatus for isolating and purifying nucleic acid using a single surface, and more particularly, a method of performing cell concentration, cell disruption and DNA purification using a single surface.

2. Description of the Related Art

In general, to extract DNA from a clinical sample, processes of concentrating target cells in a sample, disrupting the concentrated cells, and isolating and/or purifying DNA released from the disrupted cells have to be performed. To perform such processes on a solid support, surfaces having different chemical functional groups suitable for each operation have to be used. However, in general, a surface useful for cell concentration and a surface useful for DNA purification required different functional groups. Therefore, in order to use such surfaces having different functional groups suitable for each operation in a lab-on-a-chip ("LOC"), separate chambers having surfaces appropriate to each operation need to be manufactured, resulting in a complicated system and method of manufacture. In addition, a plurality of pumps and valves are required to flow fluids into each chamber, further complicating the system. Therefore, there is a need for a single surface that can both bind cells in a clinical sample and DNAs released from the sample.

U.S. Pat. No. 6,617,105 discloses a method of isolating nucleic acid from a sample containing cells, the method comprising: binding cells in the sample to a solid support coated with a cell binding moiety; disrupting the isolated cell; binding nucleic acid released from the disrupted cells to the solid support; and recovering the nucleic acid from the solid support. However, in U.S. Pat. No. 6,617,105, chaotropic salts or detergents are used for cell disruption, and a method disclosed in U.S. Pat. No. 5,234,809 is used for nucleic acid purification. U.S. Pat. No. 5,234,809 discloses a process for isolating nucleic acids from a nucleic acid-containing starting material, comprising mixing the starting material, a chaotropic substance and a nucleic acid binding solid phase, separating the solid phase with the nucleic acid bound thereto from the liquid, and washing the solid phase nucleic acid complexes. Therefore, the inventors of the present invention have earnestly studied to solve the problems of the prior art, and found that a single surface comprising a compound having a hydrophobic moiety for cell separation and a pH dependent charge switching moiety for nucleic acid purification permits efficient isolation of cells and subsequent isolation of nucleic acids released from the cells, thus completing the present invention.

SUMMARY OF THE INVENTION

The present invention provides a method of isolating nucleic acid from a cell using a single surface to which a compound having a hydrophobic moiety for cell separation and a pH dependent charge switching moiety for nucleic acid purification is bound, wherein cell concentration, cell disruption and nucleic acid purification can be efficiently performed on the single surface. The method comprises: mixing a sample containing cells with a solution comprising beads dispersed in a binding buffer to bind the cells to the beads; separating the beads having the cells bound thereto from the binding buffer and then washing the beads with a wash buffer; disrupting the cells to release nucleic acids to bind the beads; and eluting bound nucleic acid from the beads using an elution buffer, wherein a compound represented by Formula 1 below is bound to the surface of the beads:

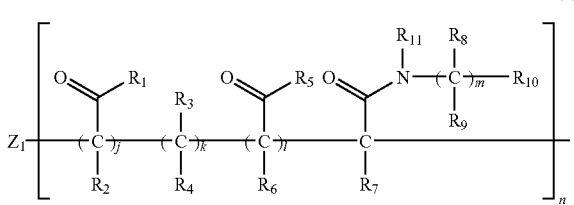

Formula (1)

where $Z_1$ is a carboxyl group or an amino group;

$R_1$, $R_2$, $R_3$, $R_5$, $R_6$, $R_7$, $R_8$, $R_9$ and $R_{11}$ are each independently selected from the group consisting of a hydrogen atom, a halogen atom, a hydroxyl group, a substituted or unsubstituted C1-C20 alkyl group, a substituted or unsubstituted C1-C20 alkoxy group, a substituted or unsubstituted C2-C20 alkenyl group, a substituted or unsubstituted C6-C30 aryl group, and a substituted or unsubstituted C6-C30 aryloxy group;

$R_4$ is a substituted or unsubstituted C4-C20 alkyl group, a substituted or unsubstituted C4-C20 alkoxy group, a substituted or unsubstituted C4-C20 alkenyl group, a substituted or unsubstituted C6-C30 aryl group, or a substituted or unsubstituted C6-C30 aryloxy group;

$R_{10}$ is a nitrogen-containing heteroaryl or heterocyclic group of 3-30 carbon atoms;

j, k, l and m are each independently an integer in the range of 1-10; and n is an integer in the range of 1-30,000.

The present invention also provides an apparatus for isolating nucleic acid from a cell using a single surface to which a compound having a hydrophobic moiety for cell separation and a pH dependent charge switching moiety for nucleic acid purification is bound, wherein cell concentration, cell disruption and nucleic acid purification can be efficiently performed on the single surface. The apparatus comprises a cell disruption micro chamber having a sample inlet through which a sample is introduced; a bead dispersion storage part in fluid communication with the cell disruption micro chamber which supplies a bead dispersion to the micro chamber; a binding buffer storage part in fluid communication with the cell or virus disruption micro chamber which supplies a binding buffer to the micro chamber; a nucleic acid eluting buffer storage part in fluid communication with the cell disruption micro chamber which supplies a nucleic acid eluting buffer to the micro chamber; and a laser generation part attached to the cell disruption micro chamber which irradiates the micro chamber with a laser.

The present invention also provides a lab-on-a-chip including the apparatus.

The present invention also provides a bead for isolating nucleic acid from a cell, wherein a compound represented by Formula 1 is bound to the surface of the bead.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
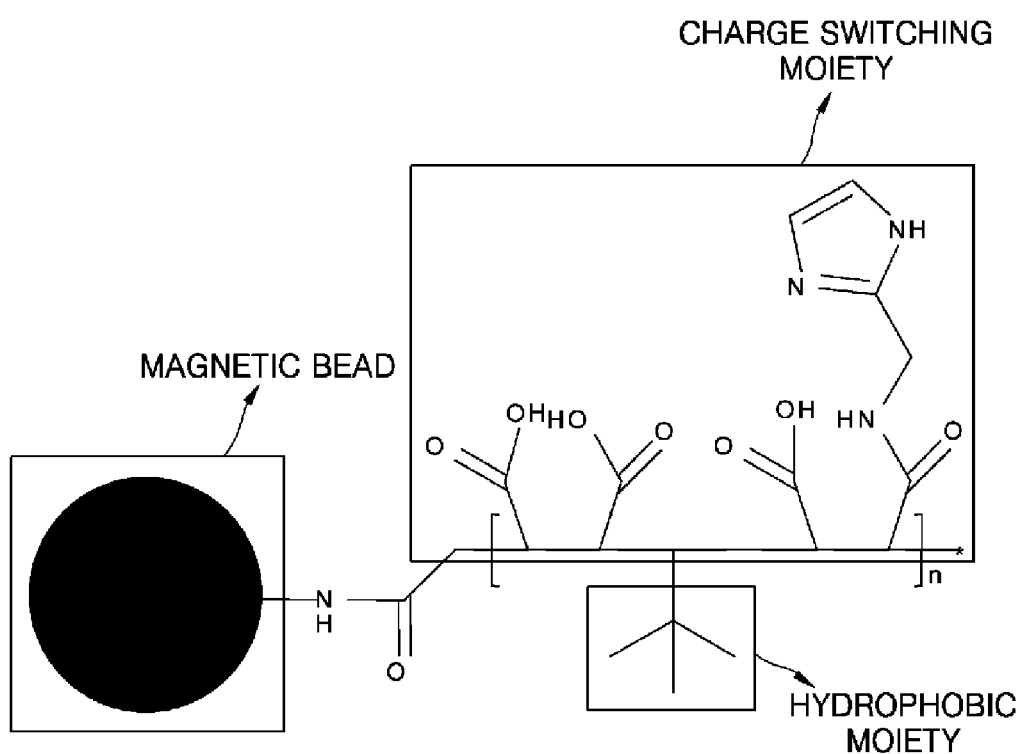
FIG. 1 illustrates a bead used in the method according to an embodiment of the present invention.

According to an embodiment of the present invention, there is provided a method of isolating and purifying nucleic acid from cells, the method comprising: mixing a sample containing cells with a solution comprising beads dispersed in a binding buffer to bind the cells onto the beads; separating the beads having the cells bound thereto from the binding buffer and then washing the beads with a wash buffer; disrupting the bound cells to release nucleic acid such that the nucleic acid binds to the beads; optionally washing the beads having nucleic acid bound thereto with the wash buffer; and eluting bound nucleic acid from the beads using an elution buffer, wherein a compound represented by Formula 1 below is bound to the surface of the beads:

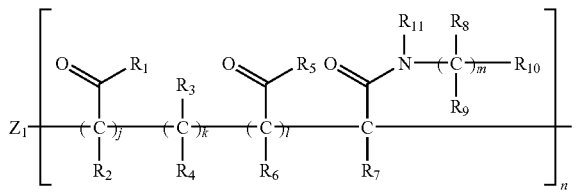

Formula (1)

where $Z_1$ is a carboxyl group or an amino group;

$R_1$, $R_2$, $R_3$, $R_5$, $R_6$, $R_7$, $R_8$, $R_9$ and $R_{11}$ are each independently selected from the group consisting of a hydrogen atom, a halogen atom, a hydroxyl group, a substituted or unsubstituted C1-C20 alkyl group, a substituted or unsubstituted C1-C20 alkoxy group, a substituted or unsubstituted C2-C20 alkenyl group, a substituted or unsubstituted C6-C30 aryl group, and a substituted or unsubstituted C6-C30 aryloxy group;

$R_4$ is a substituted or unsubstituted C4-C20 alkyl group, a substituted or unsubstituted C4-C20 alkoxy group, a substituted or unsubstituted C4-C20 alkenyl group, a substituted or unsubstituted C6-C30 aryl group, or a substituted or unsubstituted C6-C30 aryloxy group;

$R_{10}$ is a nitrogen-containing heteroaryl or a heterocyclic group of 3-30 carbon atoms;

j, k, l and m are each independently an integer in the range of 1-10; and n is an integer in the range of 1-30,000. As used herein, the term "cell" means a prokaryotic or eukaryotic cell, a plant cell, a bacteria cell, a pathogenic cell, a yeast cell, an aggregate of cells, a virus, a fungus, or other nucleic acid containing biological material, such as, for example, an organelle.

In an embodiment, the beads used in the method have a surface that has a hydrophobic functional group that can bind cells in a clinical sample and a functional moiety that can bind DNA released from the cells under the same conditions as that for cell binding but which can release the bound DNA when the pH changes. In Formula 1, $R_4$ is a functional group corresponding to the hydrophobic moiety that can bind cells, and represents a hydrocarbon of at least 4 carbon atoms, preferably, a substituted or unsubstituted C4-C20 alkyl group, a substituted or unsubstituted C4-C20 alkoxy group, a substituted or unsubstituted C4-C20 alkenyl group, a substituted or unsubstituted C6-C30 aryl group, or a substituted or unsubstituted C6-C30 aryloxy group. In the current embodiment, when a sample containing cells is mixed with a solution comprising beads dispersed in a binding buffer, the cells are bound to the hydrophobic moiety of the compound of Formula 1 bound to the bead.

When the concentration of the cells in a sample is low because the volume of the sample is large, after the cells are bound to a bead, the bead can be separated from the sample. The bead can be separated from the sample by applying a magnet or an electromagnetic field to the sample, or by centrifugation or the like, but the method of separating the beads is not limited thereto. After separation from the sample, the beads can be dispersed in the binding buffer, or in any other buffer suitable for lysing the cells. At this time, the volume of buffer into which the beads are placed can be very small, for example, about 5 μl.

Cells bound to the dispersed beads are disrupted by laser-irradiation or heating. For disrupting the cells, heating can be performed at 94-96° C. for 3-10 minutes.

When laser-irradiation is used to disrupt the bound cells, beads that absorb a laser beam, for example, magnetic beads, can be used. Laser-irradiation of a solution containing magnetic beads causes cell ablation on the beads, due to the transfer of shock waves, vapor pressure and heat to the cell surfaces as a result of the energy of the laser beam. At the same time, physical shocks are also applied to the cell surfaces. The magnetic beads are heated by the laser, raise the temperature of the solution, and directly disrupt the cells. The magnetic beads in the solution do not act simply as a heat conductor; but in addition they apply thermal, mechanical and physical shocks to the cell surface, thereby efficiently disrupting the cells.

The term "magnetic bead" as used herein means that the bead is capable of having a magnetic moment imparted to it when placed in a magnetic field, and thus is displaceable under the action of that field.

The laser beam used to irradiate the beads can be generated by a pulse laser or a continuous wave (CW) laser. The laser power is about 10 mW or more for the CW laser and about 1 mJ/pulse or more for the pulse laser. Preferably, the pulse laser has a power of about 3 mJ/pulse or more and the CW laser has a power of about 100 mW or more. Laser ablation cannot effectively occur if the laser power is too low. When the power of the CW laser is less than about 10 mW or the power of the pulse laser is less than about 1 mJ/pulse, insufficient energy to disrupt the cells is transferred.

The laser beam is generated in a specific wavelength range in which magnetic beads can absorb the energy of the laser. The laser beam is generated preferably in the wavelength range of about 400 nm or higher, and more preferably in the wavelength range from about 750 nm to about 1,300 nm. In an embodiment, the laser beam is generated in a wavelength range in which DNA is not damaged or denatured. DNA can be denatured or damaged when the wavelength of the laser is less than about 400 nm. The laser beam can also be generated in one or more wavelengths. That is, the laser can have one wavelength or two or more different wavelengths within the above range.

The diameter of the magnetic beads is preferably from about 50 nm to about 1,000 μm, and more preferably from about 1 μm to about 50 μm. When the diameter of the magnetic beads is less than about 50 nm, physical and mechanical shocks are insufficient to cause cell lysis. When the diameter of the magnetic beads is greater than about 1,000 μm, it is not suitable for LOC. The magnetic beads can also be a mixture of beads with two or more sizes. That is, the magnetic beads can be of the same size or can be a mixture of beads of different sizes.

When cells are disrupted, for example by irradiation with a laser beam, nucleic acids are released from the cells. The nucleic acids are bound to the beads via the DNA binding moiety of the compound represented by Formula I bound to the beads. In Formula 1, $R_{10}$ is a functional group corresponding to a DNA binding moiety. $R_{10}$ is a nitrogen-containing heteroaryl or heterocyclic group of C3-C30; preferably, it is a pyridinyl group or an imidazolyl group.

Subsequently, the beads having nucleic acid bound thereto can be washed with a wash buffer. As a result, impurities that are not bound to the bead, for example, cell debris or proteins can be removed. The wash buffer can be the binding buffer, or any other buffer suitable for removal of the impurities without removing the bound nucleic acid.

To elute purified nucleic acid, a nucleic acid elution buffer can be added to the beads Irradiating the beads with a laser beam or heating the beads can be simultaneously performed with addition of the elution buffer to increase the efficiency of eluting the bound nucleic acid from the beads.

The surface of the bead has a compound represented by Formula 1 bound thereto. In a compound according to an embodiment of the present invention, a carboxyl group or an amino group represented by $Z_1$, can be bound to the bead by a peptide bond.

In Formula 1 above, $R_1$ and $R_5$ can each be a hydroxyl group. When $R_1$ and $R_5$ are each a hydroxyl group, they are each a part of a carboxylic acid which can function as a nucleic acid eluting moiety, depending on pH.

FIG. 1 illustrates a bead used in the method according to an embodiment of the present invention. In FIG. 1, the bead is a magnetic bead, and within the charge-switching moiety of the compound of Formula 1, a DNA binding moiety is an imidazolyl group, and a DNA releasing moiety is a carboxyl group.

According to an embodiment of the present invention, $R_1$, $R_2$, $R_3$, $R_5$, $R_6$, $R_7$, $R_8$, $R_9$ and $R_{11}$ of the compound represented by Formula I can each comprise an alkyl group that has a straight or branched radical of C1-C20, preferably, a straight or branched radical of C1-C12. Preferably, the alkyl radical is a lower alkyl radical having 1-6 carbon atoms. Examples of the alkyl radical include methyl, ethyl, n-propyl, isopropyl, n-butyl, isobutyl, sec-butyl, t-butyl, amyl, iso-amyl, hexyl or the like. More preferably, the alkyl radical is a lower alkyl radical having 1-3 carbon atoms.

According to an embodiment of the present invention, $R_1$, $R_2$, $R_3$, $R_5$, $R_6$, $R_7$, $R_8$, $R_9$ and $R_{11}$ of the compound represented by Formula I can each comprise an alkoxy group that is an oxygen-containing straight or branched radical including an alkyl part of C1-C20. Preferably, the alkoxy radical is a lower radical having 1-6 carbon atoms. Examples of the alkoxy radical include methoxy, ethoxy, propoxy, butoxy and t-butoxy. More preferably, the alkoxy radical is a lower alkoxy radical having 1-3 carbon atoms. The alkoxy radical can be a haloalkoxy radical that is substituted with at least one halo atom such as fluoro, chloro or bromo. More preferably, the haloalkoxy radical is a lower haloalkoxy radical having 1-3 carbon atoms. Examples of the haloalkoxy radical include fluoromethoxy, chloromethoxy, trifluoromethoxy, trifluoroethoxy, fluoroethoxy and fluoropropoxy.

According to an embodiment of the present invention, $R_1$, $R_2$, $R_3$, $R_5$, $R_6$, $R_7$, $R_8$, $R_9$ and $R_{11}$ of the compound represented by Formula I can each comprise an alkenyl group that has a carbon-carbon double bond and a C2-C30 straight or branched aliphatic hydrocarbon. The alkenyl group may preferably have 2-12 carbon atoms within a ring, more preferably, 2-6 carbon atoms within a ring. The term "branched" represents that at least one lower alkyl group or lower alkenyl group is attached to the straight chain of the alkenyl group. The alkenyl group can be unsubstituted, or can be independently substituted by at least one functional group which includes halo, carboxy, hydroxyl, fomyl, sulfo, sulfino, carbamoyl, amino and imino, but is not limited thereto. Examples of the alkenyl group include ethenyl, prophenyl, carboxyethenyl, carboxyprophenyl, sulfinoethenyl and sulfonoethenyl.

The aryl group as used herein, which is used alone or in combination, refers to a carbocyclic aromatic system of 6-20 carbon atoms having one or more rings. The rings may be attached to each other as a pendant group or may be fused. The term "aryl" includes an aromatic radical such as phenyl, naphthyl, tetrahydronaphthyl, indane, and biphenyl. Phenyl is more preferable. The aryl group may have 1-3 substituents such as hydroxy, halo, haloalkyl, nitro, cyano, alkoxy, and lower alkylamino.

The aryloxy group as used herein refers to aryl-O—. The definition of the "aryl" in the aryloxy group is as described above.

In the method according to an embodiment of the present invention, the binding buffer can have a pH of about 3 to about 5. When the pH of the binding buffer is beyond this range, binding efficiency between cells or nucleic acids and the beads is decreased. The binding buffer can be phosphate buffer, acetate buffer, citrate buffer, MES buffer or the like, but is not limited thereto. The binding buffer may have a concentration of about 10 to about 1,000 mM. When the concentration of the binding buffer is less than the lower end of this range, efficiency of binding of cells or nucleic acids to the beads and efficiency of washing impurities, such as cell debris or proteins, from the beads are reduced. When the concentration of the binding buffer is greater than the higher end of this range, preparation of the binding buffer is difficult.

In the method according to an embodiment of the present invention, the nucleic acid elution buffer may have a pH of about 8 to about 10. When the pH of the nucleic acid elution buffer is less than the lower end of this range, eluting efficiency of nucleic acid is reduced. When the pH of the nucleic acid elution buffer is greater than the higher end of this range, subsequent processes can be affected. The nucleic acid elution buffer can be phosphate buffer, HEPES buffer, Tris buffer or the like, but is not limited thereto. The nucleic acid elution buffer may have a concentration of about 10 to about 1,000 mM. When the concentration of the nucleic acid elution buffer is outside this range, eluting efficiency of nucleic acid from the beads is reduced, and subsequent processes can be also affected.

In the method according to an embodiment of the present invention, the bead can be a magnetic bead, a silica bead, a polystyrene bead, a glass bead, a cellulose bead or the like, but is not limited thereto. Preferably, the bead is a magnetic bead when laser-irradiation is used for disrupting cells bound to the beads, since magnetic beads can absorb energy from the laser. On the other hand, when beads that do not absorb energy from a laser are used, for example, a silica bead, a polystyrene bead, a glass bead, or a cellulose bead, disruption of cells can be performed by heating.

In an embodiment of the present invention, the sample containing cells can be saliva, urine, blood, serum, a cell culture or the like, but is not limited thereto. The sample can be any solution comprising nucleic acids, such as animal cells, plant cells, bacteria, viruses, phage and the like.

According to another embodiment of the present invention, there is provided an apparatus for continuously performing isolation and purification of nucleic acid, the apparatus comprising: a cell disruption micro chamber having a sample inlet through which a sample containing cells is introduced; a bead dispersion storing part in fluid communication with the cell disruption micro chamber through a micro channel which supplies a bead dispersion to the micro chamber through the micro channel; a binding buffer storing part in fluid communication with the cell disruption micro chamber through a micro channel which supplies a binding buffer to the micro chamber through the micro channel; a nucleic acid elution buffer storing part in fluid communication with the cell disruption micro chamber through a micro channel which supplies a nucleic acid elution buffer to the micro chamber through the micro channel; and a laser generation part attached to the cell disruption micro chamber which supplies a laser beam to irradiate the micro chamber.

The micro chamber that disrupts cells includes an inlet through which a sample comprising cells is introduced. The sample is thoroughly mixed with beads, a process that can be achieved by various mixing methods, for example vibration. A laser beam can irradiate the mixture of the sample and the beads while vibrating the mixture. A cell disruption chamber window should be composed of a material transparent to the laser beam. Magnetic beads exposed to the laser transform light to heat, i.e. laser ablation. Heat, vibration, shock wave, vapor pressure, etc. are efficiently transferred to the cells due to effective heat transfer and collision of the magnetic beads with bound cells by continuous vibration.

The vibrator used to generate the vibration can be a sonicator, a vibrator using a magnetic field, a vibrator using an electric field, a mechanical vibrator such as a vortex etc., or a piezoelectric material. A vibrator is attached to the micro chamber and can be any device capable of vibrating the solution of the cells and the beads.

In an embodiment, the apparatus can further comprise an electromagnet that is attached to the micro chamber. The electromagnet is attached to the micro chamber to immobilize magnetic beads in a predetermined space of the micro chamber. When a sample containing cells flows over the immobilized magnetic beads in the micro chamber, the cells can bind to the magnetic beads.

In the absence of the electromagnet, extra steps have to be taken to separate the beads having cells bound thereto from the sample. For example, magnetic beads and a sample containing cells are mixed to bind the cells to the magnetic beads, the magnetic beads are next separated from the sample, and dispersed in a buffer. When an electromagnet is used, the separation process described above becomes unnecessary, and the number of steps of separating cells can be reduced. For the purpose of LOC implementation, the magnetic beads can be recovered or constrained to one position in the micro chamber by applying an electromagnet field after disruption of the cells. In so doing, nucleic acids released from the cells can be purified without a step of separating the magnetic beads from the sample, and therefore the eluted purified nucleic acid solution can directly feed into a chamber for a subsequent use, such as a Polymerase Chain Reaction ("PCR") chamber.

The apparatus according to an embodiment of the present invention can further include a nucleic acid amplification chamber in fluid communication with the micro chamber through a microchannel. For the purpose of the LOC implementation, an amplification system of the purified nucleic acid is necessary. The purified nucleic acid can be detected using a spectrophotometer, an electrochemical method, electrochemiluminescence, radiation or fluorescent labeling, a real-time PCR method, or the like. The PCR method is most suitable to sufficiently amplify a desired DNA. Other DNA amplification methods can be applied and direct detection through the real-time PCR method, etc. is also possible.

The laser generating part can generate a pulse laser or a continuous wave (CW) laser. The laser power is about 10 mW or more for the CW laser and about 1 mJ/pulse or more for the pulse laser. Preferably, the power of the pulse laser is about 3 mJ/pulse or more and the power of the CW laser is about 100 mW or more.

The laser should be generated in a specific wavelength range at which magnetic beads absorb the energy of the laser. The laser is generated preferably in the wavelength range of about 400 nm or more, and more preferably in the wavelength range from about 750 nm to about 1,300 nm. The laser can also be generated in multiple wavelengths. That is, the laser can have one wavelength or two or more wavelengths within the above range.

According to another embodiment of the present invention, there is provided a lab-on-a-chip comprising the apparatus for continuously performing nucleic acid isolation and purification. Each functional element of the apparatus for isolating and purifying nucleic acid can be designed for a process-on-a-chip, furthermore, the lab-on-a-chip can be designed using known microfluidic techniques and MEMS devices.

According to another embodiment of the present invention, there is provided a bead for isolating and purifying nucleic acid from cells, wherein a compound represented by Formula 1 below is bound to the surface of the bead.

Formula (1)

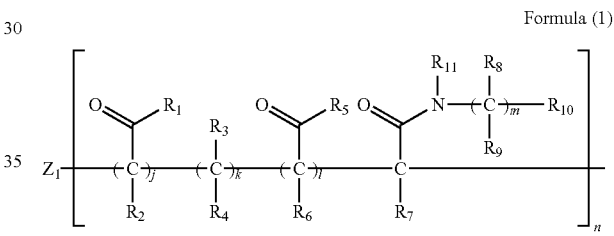

where $Z_1$ is a carboxyl group or an amino group;

$R_1$, $R_2$, $R_3$, $R_5$, $R_6$, $R_7$, $R_8$, $R_9$ and $R_{11}$ are each independently selected from the group consisting of a hydrogen atom, a halogen atom, a hydroxyl group, a substituted or unsubstituted C1-C20 alkyl group, a substituted or unsubstituted C1-C20 alkoxy group, a substituted or unsubstituted C2-C20 alkenyl group, a substituted or unsubstituted C6-C30 aryl group, and a substituted or unsubstituted C6-C30 aryloxy group;

$R_4$ is a substituted or unsubstituted C4-C20 alkyl group, a substituted or unsubstituted C4-C20 alkoxy group, a substituted or unsubstituted C4-C20 alkenyl group, a substituted or unsubstituted C6-C30 aryl group, or a substituted or unsubstituted C6-C30 aryloxy group;

$R_{10}$ is a nitrogen-containing heteroaryl or a heterocyclic group of 3-30 carbon atoms;

j, k, l and m are each independently an integer in the range of 1-10; and n is an integer in the range of 1-30,000.

In the bead according to the current embodiment of the present invention, $R_{10}$ can be a pyridinyl group or an imidazolyl group, and each of $R_1$ and $R_5$ can be a hydroxyl group.

The present invention will now be described in greater detail with reference to the following examples. The following examples are for illustrative purposes only and are not intended to limit the scope of the invention.

EXAMPLES

Example 1

Bead Surface Treatment

1) Coupling of Polyanhydrides (A Functional Group was Introduced for Introducing a Hydrophobic Functional Group and an Ionizable Functional Group)

1 ml of magnetic beads having an amine functional group, DYNABEADS M-270 Amine (Invitrogen), was washed with 1 ml of N-methyl-2-pyrolidone (NMP) three times. The magnetic beads were separated from the solution using a magnet, and then 1 ml of 200 mM (based on a repeating unit) polyanhydride (poly(isobutyl-alt-maleic anhydride)) having an average molecular weight of 50,000, dissolved in NMP, was added to the magnetic beads. Thereafter, the beads and the polyanhydride were mixed for one hour to obtain the resulting product and then washed with NMP three times.

2) Introduction of a Positive Ionizable Group

The solvent was removed from the magnetic bead solution of process 1). Then, 1 ml of a solution of 3 mM 1-(3-aminopropyl)imidazole and 6 mM triethylamine dissolved in NMP was added to the magnetic beads. The beads and the solution were mixed for one hour, and then washed with NMP three times.

3) Introduction of a Negative Ionizable Group

The solvent was removed from the resulting magnetic bead solution of process 2). 1 ml of a 0.01 N NaOH solution was added to the magnetic beads. Then, the beads and the NaOH solution were mixed for 30 minutes and washed with 1 ml of distilled water five times. Lastly, the resulting product was dispersed in 1 ml of sterilized triple distilled water and cold stored (4° C.).

Example 2

Cell Concentration using the Method According to an Embodiment of the Present Invention 50 µl a of the solution comprising beads dispersed in distilled water (prepared in Example 1) was washed twice with 100 µl a of a cell binding buffer (100 mM sodium acetate, pH 4.0) and then dispersed in 100 µl a of the same buffer. 10 µl of E. coli BL21 ($OD_{600}$=1.0) in 1× phosphate buffered saline (PBS) was mixed with 40 µl a of a 1× PBS buffer, 40 µl a of urine, or 40 µl a of blood, respectively. Then, each of the resulting samples was mixed with a prepared bead solution for two minutes. Subsequently, the beads were separated from the sample using a magnet. A sample of each cell solution, without mixing with the beads, was diluted 1/10,000 in 1×PBS. Similarly, each cell solution recovered after mixing with the beads was diluted 1/10,000 in 1×PBS. Then, an aliquot of the diluted cell solutions was plated on 3 M Petri film and the number of colonies were counted to calculate binding efficiency. The results are shown below in Table 1.

TABLE 1

| Sample | PBS buffer | Urine | Blood |
| --- | --- | --- | --- |
| Binding Efficiency | >99% | >99% | 25.0 ± 5.7% |

As can be seen in Table 1, in the PBS buffer and urine, E. coli cells were efficiently bound to the beads. However, binding efficiency of E Coli cells to the beads in blood to was relatively low. It is considered that this is because a relatively large amount of material exists in the blood inhibits E coli cells from binding to the beads.

Example 3

Cell Disruption and Nucleic Acid Purification using the Method According to an Embodiment of the Present Invention The beads bound with E. coli cells of Example 2 were dispersed in 5 µl a of a binding buffer, and the resulting solution was placed in a microchip for a TMC-1000 (Samsung Techwin). Then, the bead solution was irradiated with a laser (Hamamatsu 8446-72, 1.5 W, 808 nm) for 40 seconds. The bead solution was then removed from the microchip to quantify DNA using PICOGREEN. The beads resulting from the above procedures were dispersed in 5 µl a of the binding buffer (100 mM sodium acetate buffer, pH 4.0), and mixed for one minute. Then, the beads were removed from the binding buffer and dispersed in 5 µl a of an elution buffer (100 mM Tris, pH 9.5). The resulting solution of beads in the elution buffer was placed in a microchip for a TMC-1000 (Samsung Techwin). The solution was irradiated for 40 seconds with a 1.5 W laser, and then the elution buffer was collected to quantify the eluted DNA using PICOGREEN. The results of quantification of DNA existing in the solutions before DNA elution (after cell disruption) and after DNA elution are shown in Table 2 below.

TABLE 2

| Sample | PBS buffer | Urine |
| --- | --- | --- |
| After cell disruption | <0.1 ng/µl | <0.1 ng/µl |
| After DNA elution | 6.1 ± 1.1 ng/µl | 5.0 ± 0.9 ng/µl |

As can be seen in Table 2, since little DNA exists in the binding buffer before nucleic acids are eluted from the beads, most of the DNA is bound to the beads after cell disruption. In addition, it can be seen that a large amount of DNA is recovered from the beads using the elution buffer.

Therefore, it is confirmed that after cells bound to beads are disrupted, nucleic acids released from the cells can be eluted from the beads using a buffer that has a different pH from that of the binding buffer.

Example 4

Purity Measurement of the Purified Nucleic Acid using the Method According to an Embodiment of the Present Invention Values of $A_{260}/A_{280}$ for the eluted DNA solution of Example 3 were measured using a NANODROP (NanoDrop Technology). An experiment was performed as a control in which only cell disruption was performed without nucleic acid purification. 5 µl a of a 1×PBS buffer containing E. coli ($OD_{600}$=2.0) was added to 100 µl a of beads (Dynabead® MyOne™ carboxylic acid; Invitrogen). The bead-cell mixture was irradiated for 40 seconds with a laser beam, and then the buffer solution was separated from the beads prior to measuring $A_{260}/A_{280}$ in order to prevent interference of the beads in the spectroscopic measurements. Values of $A_{260}/A_{280}$ with respect to samples of the present invention in which DNA purification was performed after cell disruption and samples of the control in which DNA purification was not performed are shown in Table 3 below.

TABLE 3

| Sample | Example 3 sample | Control |
|---|---|---|
| $A_{260}/A_{280}$ | 1.92 ± 0.10 | 2.74 ± 0.34 |

As can be seen in Table 3, a sample obtained using the method of the present invention has a value of $A_{260}/A_{280}$ in the range of 1.8-2.0. Therefore, it can be seen that the sample obtained using the method of the present invention is purer than the control in which no nucleic acid purification process was performed.

Example 5

Real-Time PCR using Nucleic Acid Purified by the Method According to an Embodiment of the Present Invention To additionally confirm the effect of DNA purification, a real-time PCR was performed using the DNA solution prepared in Example 3. A PCR master mixture was prepared containing 2× PCR buffer (150 mM Tris-HCl (pH 9.0), 30 mM Ammonium sulfate, 5 mM gCl$_2$, and 0.2 mg/ml Bovine Serum Albumin ("BSA"); Solgent, Korea), 0.6 U/μl a of Taq polymerase (Solgent), 0.4 mM of dNTP, 0.4 μM of a forward primer, 0.4 μM of a reverse primer, 10 mM of MgCl$_2$, and 2× (relative to what concentration is this fluorophore 2×?) SYBR-green. Then, the PCR master mixture was mixed with the DNA solution prepared in Example 3 in a ratio of 1:1, and PCR was performed using the TMC-1000. Conditions of PCR were as follows: initial denaturation at 94° C. for one minute, and then 40 cycles of 94° C. for 5 seconds, 62° C. for 5 seconds, and 72° C. for 40 seconds. The region to be amplified is the 16 s rRNA gene, and the primer sequences used are as follows.

```
Forward primer:
5'-YCC AKA CTC CTA CGG GAG GC-3'      (SEQ ID NO: 1)

Reverse primer:
5'-GTA TTA CCG CTT CTG CTG GCA C-3'   (SEQ ID NO: 2)
```

Table 4 below represents results of real-time PCR performed using DNAs with or without DNA purification as measured by Ct. Ct represents the cycle number at which a fluorescence signal became detectable in the real-time PCR. That is, the higher the initial concentration of DNA in the reaction sample used for the PCR, the earlier the fluorescence signal can be detected in the real time PCR (i.e. fluorescence signals can be detected at a lower Ct value). Ct is also related to the purity of the DNA used in the real time PCR. That is, the purer the DNA, the lower the Ct value.

TABLE 4

| Sample | Ct for Urine | Ct for PBS buffer |
|---|---|---|
| Present Invention (purified) | 19.86 ± 0.59 | 23.92 ± 0.32 |
| Control (not purified) | 27.08 ± 1.54 | 33.86 ± 0.88 |

As can be seen in Table 4, samples of the present invention in which DNA purification is performed have much lower Ct values than those of samples of the control regardless of sample type, due to the effect of DNA purification using the method of the present invention.

Therefore, it is confirmed that DNA subjected to the method of the present invention is purer than DNA in a control sample which was not subjected to the method of the present invention.

After PCR was completed, the solution was removed from the chip to analyze the PCR product using a LabChip (Aglient). Table 5 represents results of real-time PCR using DNA purified (by the method of the present invention) and unpurified (control) DNA.

TABLE 5

| Sample | Urine | PBS buffer |
|---|---|---|
| Present Invention (purified) | 13.9 ± 1.7 ng/μl | 11.9 ± 3.7 ng/μl |
| Control (not purified) | 7.8 ± 1.7 ng/μl | 1.9 ± 0.5 ng/μl |

As can be seen in Table 5, samples of the present invention in which DNA was purified produced much more amplicon compared with samples of a control regardless of sample type.

According to the method of the present invention, cell concentration, cell disruption and DNA purification can be performed using the same surface that can bind cells and DNAs under the same condition. Since the whole process is performed using the same beads, a system can be easily manufactured, and can be also widely used in CDs, microchips and the like.

While the present invention has been particularly shown and described with reference to exemplary embodiments thereof, it will be understood by those of ordinary skill in the art that various changes in form and details may be made therein without departing from the spirit and scope of the present invention as defined by the following claims.

The terminology used herein is for the purpose of describing particular embodiments only and is not intended to be limiting of the invention. The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to").

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein.

Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. While the present invention has been particularly shown and described with reference to exemplary embodiments thereof, it will be understood by those of ordinary skill in the art that various changes in form and details may be made therein without departing from the spirit and scope of the present invention as defined by the following claims.

unsubstituted C2-C20 alkenyl group, a substituted or unsubstituted C6-C30 aryl group, and a substituted or unsubstituted C6-C30 aryloxy group;

$R_4$ is a substituted or unsubstituted C4-C20 alkyl group, a substituted or unsubstituted C4-C20 alkoxy group, a substituted or unsubstituted C4-C20 alkenyl group, a substituted or unsubstituted C6-C30 aryl group, or a substituted or unsubstituted C6-C30 aryloxy group;

$R_{10}$ is a nitrogen-containing heteroaryl or heterocyclic group of 3-30 carbon atoms;

What is claimed is:

1. A bead for isolating nucleic acid from cells, comprising a material represented by Formula 1 below bound to the surface of the bead:

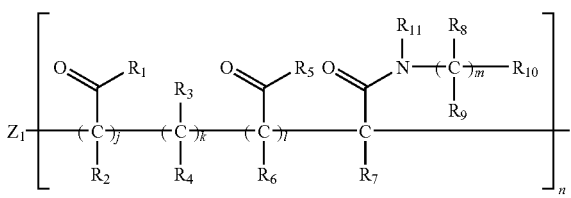

Formula (1)

where $Z_1$ is a carboxyl group or an amino group;

$R_1$, $R_2$, $R_3$, $R_5$, $R_6$, $R_7$, $R_8$, $R_9$ and $R_{11}$ are each independently selected from the group consisting of a hydrogen atom, a halogen atom, a hydroxyl group, a substituted or unsubstituted C1-C20 alkyl group, a substituted or unsubstituted C1-C20 alkoxy group, a substituted or j, k, l and m are each independently an integer in the range of 1-10; and n is an integer in the range of 1-30,000.

2. The bead of claim 1, wherein $R_{10}$ is a pyridinyl group or an imidazolyl group.

3. The bead of claim 1, wherein $R_1$ and $R_5$ are each a hydroxyl group.

4. A method of making a bead surface for isolating nucleic acid from cells, comprising:

reacting a bead with a compound to introduce a hydrophobic functional group, wherein the hydrophobic functional group is a substituted or unsubstituted C4-C20 alkyl group, a substituted or unsubstituted C4-C20 alkoxy group, a substituted or unsubstituted C4-C20 alkenyl group, a substituted or unsubstituted C6-C30 aryl group, or a substituted or unsubstituted C6-C30 aryloxy group;

reacting the bead with a second compound to introduce a charge switching moiety, wherein the charge switching moiety is a nitrogen-containing heteroaryl or heterocyclic group of 3-30 carbon atoms.

* * * * *